(12) United States Patent
Beaurain et al.

(10) Patent No.: US 9,265,619 B2
(45) Date of Patent: Feb. 23, 2016

(54) INTERVERTEBRAL DISC PROSTHESIS

(71) Applicant: LDR Medical, Rosières Près Troyes (FR)

(72) Inventors: Jacques Beaurain, Saulon la Chapelle (FR); Jean-Marc Fuentes, Grabels (FR); Jean-Marc Vital, Bordeaux (FR); Thierry Dufour, Olivet (FR); Jean Huppert, L'Etrat (FR)

(73) Assignee: LDR Medical, Rosieres Pres Troyes (FR)

( * ) Notice: Subject to any disclaimer, the term of this patent is extended or adjusted under 35 U.S.C. 154(b) by 0 days.

(21) Appl. No.: 14/306,785

(22) Filed: Jun. 17, 2014

(65) Prior Publication Data

US 2014/0364949 A1 Dec. 11, 2014

Related U.S. Application Data

(63) Continuation of application No. 13/616,448, filed on Sep. 14, 2012, now Pat. No. 8,753,397, which is a continuation of application No. 12/424,364, filed on Apr. 15, 2009, now Pat. No. 8,267,999, which is a continuation of application No. 10/533,846, filed as application No. PCT/IB03/04872 on Oct. 31, 2003, now Pat. No. 7,682,396.

(30) Foreign Application Priority Data

Nov. 5, 2002 (FR) ...................................... 02 13833

(51) Int. Cl.
*A61F 2/44* (2006.01)
*A61B 17/064* (2006.01)
*A61F 2/08* (2006.01)
*A61F 2/30* (2006.01)

(52) U.S. Cl.
CPC ............... *A61F 2/4425* (2013.01); *A61F 2/442* (2013.01); *A61B 17/0642* (2013.01); *A61B 17/0644* (2013.01); *A61B 2017/0647* (2013.01); *A61F 2/0811* (2013.01); *A61F 2002/0882* (2013.01); *A61F 2002/30354* (2013.01); *A61F 2002/30365* (2013.01); *A61F 2002/30369* (2013.01); *A61F 2002/30393* (2013.01); *A61F 2002/30397* (2013.01); *A61F 2002/30398* (2013.01);

(Continued)

(58) Field of Classification Search
CPC .......... A61F 2/44; A61F 2/4425; A61F 2/443
USPC ............................................. 623/17.11–17.16
See application file for complete search history.

(56) References Cited

U.S. PATENT DOCUMENTS 6,610,093 B1 * 8/2003 Pisharodi .................... 623/17.15

*Primary Examiner* — Andrew Yang
(74) *Attorney, Agent, or Firm* — Denko Lauff LLP

(57) ABSTRACT

The present invention relates to an intervertebral disk prosthesis comprising at least three parts including a first plate, referred to as the upper plate (1), a second plate, referred to as the lower plate (2), and a core (3), the upper surface of the core (3) being in contact with at least part (10) of the lower surface of the upper plate (1) and the lower surface of the core (3) being in contact with at least part of the upper surface of the lower plate (2), and the lower plate (1) being movable at least with respect to the core (3), characterized in that there are cooperation means between the lower to plate (2) and the core (3), so as to limit or eliminate translation movements of the core (3) with respect to the lower plate (2) along an axis substantially parallel to the lower plate (2), and to limit or eliminate rotation movements of the core (3) with respect to the lower plate (2), around an axis substantially perpendicular to the lower plate (2), the planes passing through the upper (1) is and lower (2) plates forming a substantially constant angle.

14 Claims, 4 Drawing Sheets

(52) U.S. Cl.
CPC ............... *A61F2002/30472* (2013.01); *A61F 2002/30535* (2013.01); *A61F 2002/30576* (2013.01); *A61F 2002/30616* (2013.01); *A61F 2002/30662* (2013.01); *A61F 2002/30841* (2013.01); *A61F 2002/30884* (2013.01); *A61F 2002/443* (2013.01); *A61F 2220/0016* (2013.01); *A61F 2220/0025* (2013.01); *A61F 2220/0033* (2013.01); *A61F 2220/0041* (2013.01)

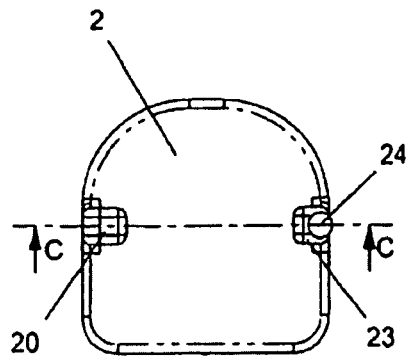
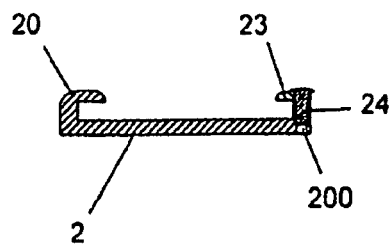
Figure 9a Figure 9b
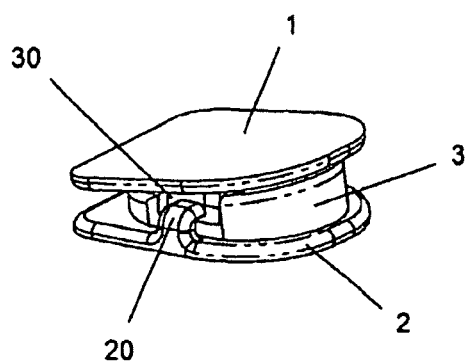
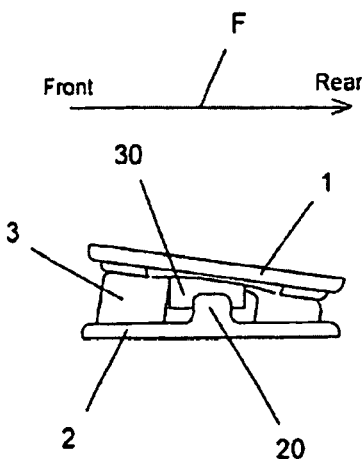
Figure 4a Figure 4b
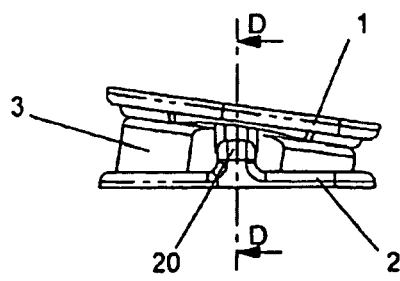
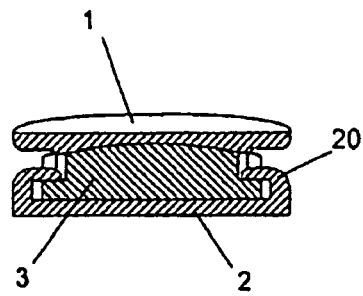
Figure 5a Figure 5b

INTERVERTEBRAL DISC PROSTHESIS

CROSS-REFERENCE TO RELATED APPLICATIONS

This application is a continuation of U.S. patent application Ser. No. 13/616,448 filed Sep. 14, 2012, and issuing as U.S. Pat. No. 8,753,397 on Jun. 17, 2014, which is a continuation of U.S. patent application Ser. No. 12/424,364 filed Apr. 15, 2009, and issuing as U.S. Pat. No. 8,267,999 on Sep. 18, 2012, which is a continuation of U.S. patent application Ser. No. 10/533,846 filed May 4, 2005, and issuing as U.S. Pat. No. 7,682,396 on Mar. 23, 2010, which is a National Stage entry of International Application PCT/IB03/004872, filed Oct. 31, 2003, which claims priority to French Patent Application No. 0213833, filed Nov. 5, 2002.

BACKGROUND

The present invention relates to an intervertebral disk prosthesis, intended to substitute the fibrocartilaginous disks joining the vertebrae in the spinal column, particularly on the cervical spine.

Various types of prosthesis are known in the prior art. Some of these prostheses, either because they are made of compressible material or because they allow excessive movement of the different constituent parts of the prosthesis with respect to each other, may induce relatively easily the ejection of at least one part of the prosthesis outside the vertebrae, which is not desirable for the patient.

SUMMARY

The purpose of the present invention is to remedy some drawbacks of the prior art by proposing a simple intervertebral disk prosthesis which makes it possible to limit the movements of the different constituent parts of the prosthesis with respect to each other.

This purpose is achieved by an intervertebral disk prosthesis comprising at least three parts including a first plate, referred to as the upper plate, a second plate, referred to as the lower plate, and a core, the upper surface of the core being in contact with at least part of the lower surface of the upper plate and the lower surface of the core being in contact with at least part of the upper surface of the lower plate, and the lower plate being movable at least with respect to the core, characterised in that there are cooperation means between the lower plate and the core, so as to limit or eliminate translation movements of the core with respect to the lower plate, along an axis substantially parallel to the lower plate, and to limit or eliminate rotation movements of the core with respect to the lower plate, around an axis substantially perpendicular to the lower plate, the planes passing through the upper and lower plates forming a substantially constant angle.

According to another feature, the lower plate comprises male means cooperating with female means of the core.

According to another feature, the lower plate comprises female means cooperating with male means of the core.

According to another feature, the angle is obtained in that the core forms an acute angle in the front-rear direction.

According to another feature, the same plates can be assembled with cores of different thicknesses.

According to another feature, the angle between the upper and lower plates is between 0.degree. and 15.degree.

According to another feature the core is movable with respect to the upper and/or lower plates, which makes it possible to compensate for positioning defects of the three parts of the prosthesis with respect to each other.

According to another feature, at least part of the lower surface of the upper plate is concave and complementary to the upper surface of the core.

According to another feature, the dimensions of each male means are slightly less than those of each female means so as to enable a slight clearance between the core and the lower plate.

According to another feature, the dimensions of each male means are substantially the same as those of each female means so as to prevent any clearance between the core and the lower plate.

According to another feature, the male means of the lower plate are two pins curved towards the inside of the prosthesis and located opposite each other on two edges of the prosthesis, and in that the female means of the core are two recesses.

According to another feature, at least one of the pins is replaced by a lug equipped with a drilling whereon a tag is fixed using a dowel entering the drilling.

According to another feature, the male means of the lower plate are two dowel pins located in the vicinity of the centre of the lower plate, and in that the female means of the core are two wells.

According to another feature, the male means of the lower plate are two walls located opposite each other in the vicinity of two edges of the prosthesis, and in that the female means of the core are recesses.

According to another feature, the male means of the lower plate are a rib located at the centre of the prosthesis, and in that the female means of the core are a groove.

According to another feature, the core is made of polyethylene.

According to another feature, the lower plate comprises one or more openings in the vicinity of its front side, provided to receive prosthesis anchoring means in a vertebra.

According to another feature, the opening of the lower plate is rectangular, and in that the anchoring means consist of a body, forming an acute angle with the lower plate, and a head.

According to another feature, the openings of the lower plate are circular, and in that the anchoring means are nail-shaped.

According to another feature, the upper plate is convex on at least part of its upper surface to fit into the shape of the vertebrae.

Other features and advantages of the present invention will be seen more clearly upon reading the description below, with reference to the appended figures, wherein:

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 9a represents a top view of the lower plate according to a fourth embodiment, FIG. 9b represents a sectional view of the lower plate along the plane plan C-C of FIG. 9a, FIGS. 10a and 10b respectively represent a rear and side view of the upper plate according to another embodiment.

DETAILED DESCRIPTION

The intervertebral disk prosthesis according to the invention is constituted of an upper plate 1 which is articulated with respect to a lower plate 2 by means of a core 3, as can particularly be seen in FIGS. 4a, 4b, 5a and 6a. One advantage of the prosthesis according to the invention is that it comprises simple parts which can be designed so that the prosthesis is fitted on the cervical spine.

Figure 1A:
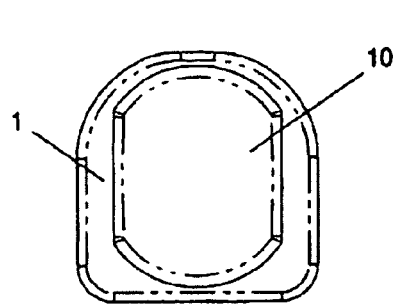
FIGS. 1a and 1b respectively represent a bottom view and a perspective bottom view of the upper plate according to one embodiment, FIGS. 2a and 2b respectively represent a top view and a perspective top view of the lower plate according to one embodiment, FIGS. 3a and 3b respectively represent a top view and a perspective top view of the core according to one embodiment, FIGS. 4a and 4b respectively represent a perspective top view and a side view of the intervertebral disk prosthesis according to the embodiment of FIGS. 1a, 1b, 2a, 2b, 3a and 3b, FIGS. 5a and 5b respectively represent a side view and a sectional view along the plane D-D of FIG. 5a of the intervertebral disk prosthesis according to a second embodiment.
Figure 1B:
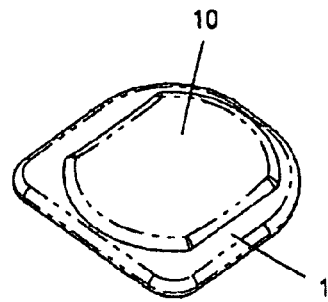
Figure 2A:
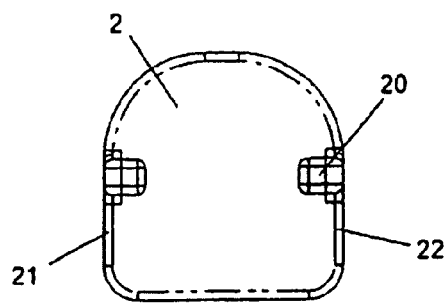
Figure 2B:
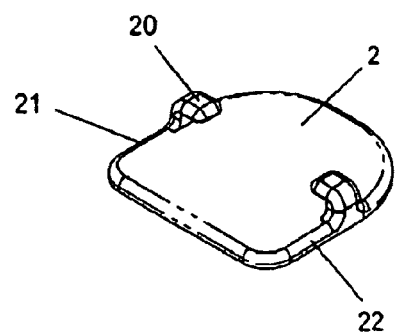

The upper plate 1, particularly visible in FIGS. 1a and 1b, is slightly concave on at least part 10 of its lower surface, so as to fit with the slightly convex upper surface of the core 3. The upper surface of the core 3 is complementary to the concave part 10 of the upper plate 1, enabling movement between the upper plate 1 and the core 3.

Figure 10A:
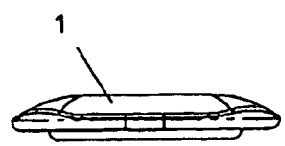
Figure 10B:
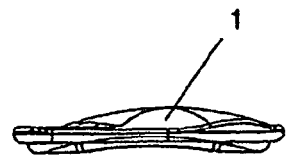

In an alternative embodiment, part of the upper surface of the upper plate 1 is convex, as shown in FIGS. 10a and 10b, in order to fit better onto the vertebra whereon the prosthesis is to be fitted, the bottom of the vertebrae being concave. In this case, the convex part of the upper plate 1 is located in the front part of the upper plate, as can particularly be seen in FIG. 10b.

Figure 3A:
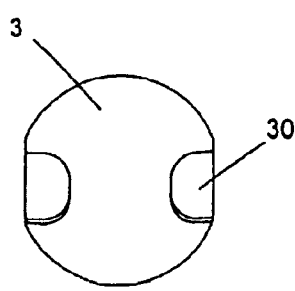
Figure 3B:
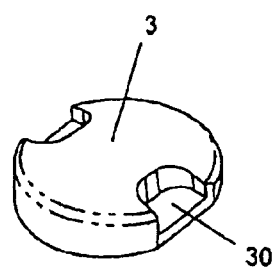
Figure 6A:
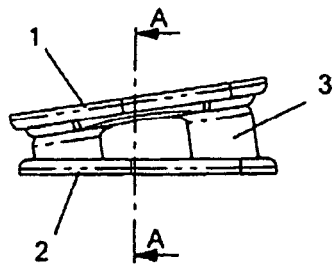
FIG. 6a represents a side view of the intervertebral disk prosthesis according to a third embodiment.
Figure 6B:
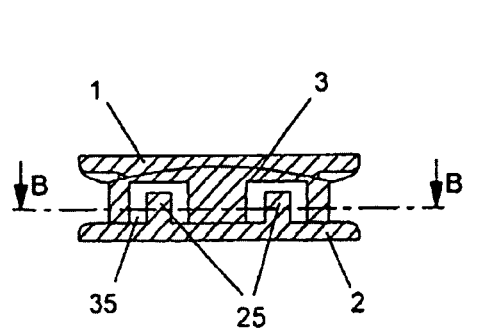
FIGS. 6b and 6d represent a sectional view along the plane A-A of FIG. 6a, the core having, respectively, a slight clearance and no clearance with respect to the lower plate.
Figure 6C:
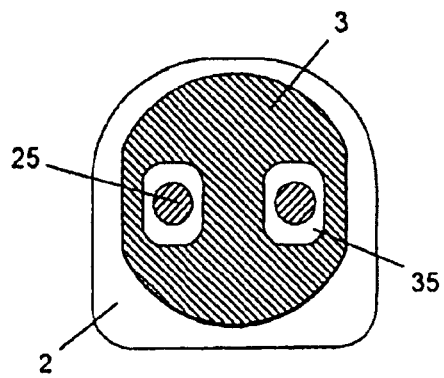
FIGS. 6c and 6e represent a sectional view along the plane B-B of FIGS. 6b and 6d, respectively, of the intervertebral disk prosthesis, FIGS. 7a and 8a respectively represent a top view and perspective bottom view of the lower plate according to two other embodiments, FIGS. 7b and 8b respectively represent a perspective side view and a perspective top view of the lower plate of FIGS. 7a and 8a, respectively, wherein prosthesis anchoring means are inserted according to two different embodiments.
Figure 6D:
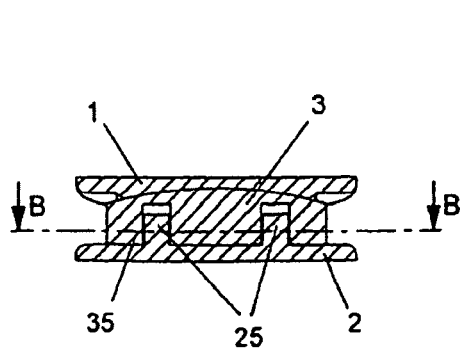
Figure 6E:
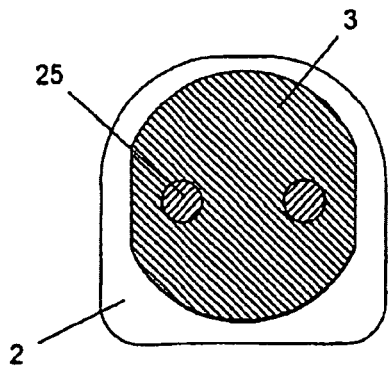

The lower plate 2 is substantially plane. In effect, its lower surface does not need to be convex or concave since the top of the vertebrae is substantially flat. In the embodiment of FIGS. 2a, 2b, 7a and 8a, the lower plate 2 comprises two pins 20 located opposite, each other on two substantially parallel edges 21, 22 of the lower plate 2. Each pin 20 is curved towards the inside of the prosthesis and can thus enter recesses 30 located on the core 3. The core 3, particularly visible in FIGS. 3a and 3b, comprises a substantially plane lower surface, provided to fit onto the lower plate 2. The core 3 is thin (for example 3 mm thick) for a cervical prosthesis or thicker (for example 15 mm) for a lumbar prosthesis.

In the embodiment of FIGS. 3a, 3b, 4a and 4b, the dimensions of each recess 30 of the core 3 are slightly greater than those of each pin 20 of the lower plate 2 so as to limit the clearance of the core 3 with respect to the lower plate 2, both in translation along an axis substantially parallel with the lower plate 2, and in rotation around an axis substantially perpendicular to the lower plate 2. The movement between the upper plate 1 and the core 3, as well as the clearance of the core 3 with respect to the lower plate 2, thus enable the patient to move and, if required, compensate for prosthesis positioning defects. This clearance also offers the advantage of preventing premature wear due to the stress applied to the prosthesis.

In the embodiment of FIGS. 5a and 5b, the dimensions of each recess 30 of the core 3 are substantially the same as those of each pin 20 of the lower plate 2, so as to prevent any clearance of the core 3 with respect to the lower plate 2, both in translation and rotation. In the latter case, the only movement of the prosthesis authorised is that of the upper plate 1 with respect to the core 3.

In the embodiment in FIGS. 9a and 9b, one of the pins 20 is replaced by a lug equipped with a drilling 200. A tag 23 fixes on the lug by means of a dowel 24 entering the drilling 200. In an alternative embodiment, both pins are replaced by a lug whereon a tag 23 is fixed.

In the embodiment of FIGS. 6a, 6b, 6c, 6d and 6e, the lower plate 2 does not comprise any pins 20 but two dowel pins 25 located in the vicinity of the centre of the lower plate 2. In this case, the core 3, by complementarity, does not comprise any recesses 30, but two wells 35 under its lower surface. The dimensions of the dowel pins 25 of the lower plate 2 and of the wells 35 of the core 3 are such that, in the alternative embodiment represented in FIGS. 6b and 6c, a slight clearance in translation and rotation is permitted, and in the alternative embodiment represented in FIGS. 6d and 6e, no clearance is permitted.

In another embodiment, not shown, the lower plate 2 comprises a rib on its upper surface and no pins 20 or dowel pins 25. The core 3, by complementarity, comprises a groove under its lower surface. The dimensions of the rib of the lower plate and the groove of the core are such that, in one alternative embodiment, a slight clearance in translation and rotation is permitted, and in another alternative embodiment, no clearance is permitted.

In another embodiment not shown, the lower plate 2 comprises, instead of the pins 20, two walls, arranged opposite each other, in the vicinity of two substantially parallel edges 21, 22 of the lower plate, but further in the prosthesis than the pins 20. The core 3 comprises complementary recesses with respect to the walls. The dimensions of each recess of the core in this embodiment are, either slightly greater, or substantially the same as those of each wall of the lower plate, so as to enable a slight clearance in translation and rotation or not.

In a further embodiment not shown, the female components are located on the lower plate and the male components on the core.

The intervertebral disk prosthesis according to the invention particularly makes it possible to correct lordosis defects and to add lordosis to the spine, for example the cervical spine. Therefore, the presence of an acute angle in the front-rear direction F. FIG. 4b, between the upper plate 1 and the lower plate 2 of the prosthesis is necessary. For example, this angle is between 0.degree. and 15.degree. To adjust the angle required according to the patient, it is simply necessary to select a core 3 with a suitable angle between the mean plane representing its upper surface and the plane passing through its lower surface.

When the female components are located on the lower plates and the male components on the core, the lordotic core, in that it forms an acute angle in the front-rear direction, may then be integral with the plate by a projection entering a cavity or opening of the lower plate.

The inclination of the prostheses known in the prior art is obtained, either by the shape of the upper plate, when the core is flat, or by the position of the upper plate with respect to the core, when said core is convex. With respect to the first case of the prior art mentioned here, the machining of the prosthesis according to the present invention is more economical since the core is composed of a less expensive material (for example, polyethylene) than that composing the plates. With respect to the second case of the prior art mentioned here, the core of the present invention is not liable to be ejected outside the prosthesis since the angle between the plates is substantially constant when the prosthesis is in place.

If surgeons require a determined lordosis for one patient, they will select a core 3 allowing no clearance with respect to the lower plate 2. On the other hand, if they simply require the lordosis to remain within a range of values, they will select a core allowing a slight clearance in translation and rotation with respect to the lower plate 2.

The intervertebral disk prosthesis according to the invention may, in one alternative embodiment, represented in FIGS. 7a, 7b, 8a and 8b, be anchored in the spinal column to prevent the prosthesis from migrating under the effect of the transversal resultant of the force exerted by the spinal column on the prosthesis in place, which increases with the lordosis. In this case, the lower plate 2 comprises one or more openings 28, 29 located in the vicinity of the rear side of the prosthesis, making it possible to receive anchoring means 4, 5.

Figure 7A:
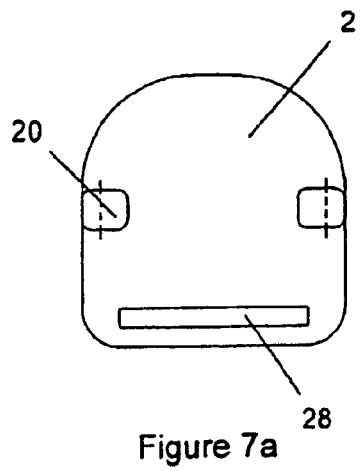
Figure 7B:
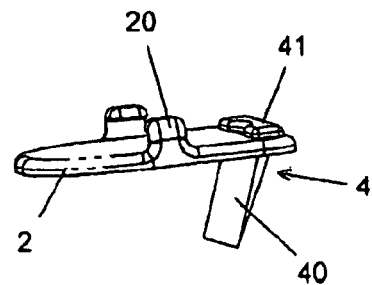

In this way, in the case of FIGS. 7a and 7b, the opening 28 of the lower plate 2 is rectangular and the anchoring means 4 is constituted of a body 40 and a head 41. The dimensions of the head 41 are slightly greater than those of the opening 28 of the lower plate 2, such that, once the anchoring means 4 are in place in a vertebra, the lower plate 2 is sandwiched between the head 41 of the anchoring means 4 and said vertebra. An angle, less than or equal to 90.degree., is comprised between the body 40 of the anchoring means 4 and the lower plate 2.

Figure 8A:
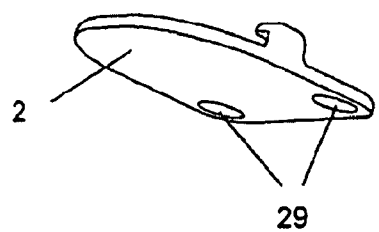
Figure 8B:
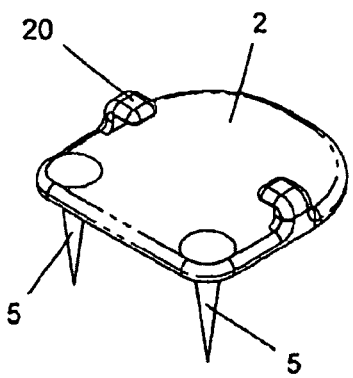

In the case of FIGS. 8a and 8b, two circular openings 29 are comprised in the lower plate 2 and the anchoring means 5 are nail-shaped, with a head of greater dimensions than those of the openings 29 to make it possible to sandwich the lower plate 2 between the head of the anchoring means 5 and the vertebra whereon the prosthesis is anchored.

It should be clear to those skilled in art that the present invention enables embodiments in numerous other specific forms without deviating from the scope of the invention as claimed. Consequently, the present embodiments must be considered as illustrations, but may be modified in the field defined by the scope of the attached claims, and the invention must not be limited to the details given above.

The invention claimed is:

1. An intervertebral disc prosthesis configured and arranged for placement between an first spinal vertebra and a second spinal vertebra, the prosthesis in its assembled and operational configuration comprising
   a first plate;
   a second plate comprising first and second lateral plate sides disposed on opposite edges of the plate, a first protrusion disposed along the first lateral plate side and extending toward the first plate, and a second protrusion disposed along the second lateral plate side and extending toward the first plate;
   a moveable core disposed between the first plate and the second plate with a surface of the core facing the second plate, the core comprising first and second lateral core sides disposed on opposite edges of the core, the first lateral core side having a first recess open to the surface of the core and open to the first lateral core side and sized to receive and allow movement of the first protrusion, and the second lateral core side having a second recess open to the surface of the core and open to the second lateral core side and sized to receive and allow movement of the second protrusion; and
   a slot in in at least one of the first and second plates, and a removable anchor having a plate-like body sized to fit the slot and a head that is larger than the slot.

2. An intervertebral disc prosthesis according to claim 1 in which the slot is configured and arranged to project the tip of the anchor away from the prosthesis at an angle.

3. An intervertebral disc prosthesis according to claim 2 in which the core forms an acute angle in a front-rear direction.

4. An intervertebral disc prosthesis configured and arranged for placement between a first vertebra and a second vertebra, the prosthesis in its assembled and operational configuration comprising:
   a mobile core having an first surface, an opposite second surface, and a perimeter extending between the first surface and the second surface, the perimeter having a front face, a rear face, a first lateral face, and a second lateral face opposite the first lateral face, and the core having a first height between the first surface and the second surface at the front face, a second height between the first surface and the second surface at the rear face, and a third height between the first surface and the second surface between the front face and the rear face, with the third height greater than the first height and the first height greater than the second height;
   a first plate having a surface configured for contact with a face of the first vertebra, an opposite surface in contact with the first surface of the core, a first lateral edge, and a second lateral edge opposite the first lateral edge;
   a second plate having a surface configured for contact with a face of the second vertebra and an opposite surface in contact with the second surface of the core;
   a first protuberance disposed along the first lateral edge of the first plate extending toward the second plate, the first protuberance having a length and a width;
   a second protuberance disposed along the second lateral edge of the first plate extending toward the second plate, second first protuberance having a length and a width;
   a first notch disposed in the core and opening on the first surface of the core and the first lateral face of the core, the first notch receiving the first protuberance and having a length greater than the length of the first protuberance and a width greater than the width of the first protuberance; and
   a second notch disposed in the core and opening on the first surface of the core and the second lateral face of the core, the second notch receiving the second protuberance and having a length greater than the length of the second protuberance and a width greater than the width of the second protuberance.

5. An intervertebral disc prosthesis according to claim 4 in which the protuberance is a pin.

6. An intervertebral disc prosthesis according to claim 4 in which the protuberance is a wall.

7. An intervertebral disc prosthesis according to claim 4 in which the protuberance is a lug.

8. An intervertebral disc prosthesis according to claim 4 comprising a slot in in at least one of the first and second plates, and a removable anchor having a plate-like body sized to fit the slot and a head that is larger than the slot.

9. An intervertebral disc prosthesis according to claim 8 in which the slot is configured and arranged to project the tip of the anchor away from the prosthesis at an angle.

10. An intervertebral disc prosthesis according to claim 4 in which the first notch does not open on second surface of the core.

11. An intervertebral disc prosthesis according to claim 10 in which the second notch does not open on second surface of the core.

12. An intervertebral disc prosthesis according to claim 4 in which the first surface of the core is convex.

13. An intervertebral disc prosthesis configured and arranged for placement between an first spinal vertebra and a second spinal vertebra, the prosthesis in its assembled and operational configuration comprising:
   a first plate;
   a second plate comprising first and second lateral plate sides disposed on opposite edges of the plate, a first protrusion disposed along the first lateral plate side and extending toward the first plate, and a second protrusion disposed along the second lateral plate side and extending toward the first plate;
   a moveable core disposed between the first plate and the second plate with a surface of the core facing the second plate, the core comprising first and second lateral core sides disposed on opposite edges of the core, the first lateral core side having a first recess open to the surface of the core and open to the first lateral core side and sized to receive and allow movement of the first protrusion, and the second lateral core side having a second recess open to the surface of the core and open to the second lateral core side and sized to receive and allow movement of the second protrusion; and an anchor projecting from the second plate, with the second plate having a slot with a generally rectangular cross-section configured and arranged to receive the anchor, and the anchor comprises a plate having a generally rectangular cross-section and a head that is larger than the generally rectangular cross-section of the slot.

14. An intervertebral disc prosthesis according to claim 13 in which the core forms an acute angle in a front-rear direction.

\* \* \* \* \*